United States Patent [19]
Mauze

[11] Patent Number: 5,628,311
[45] Date of Patent: May 13, 1997

[54] CHEMICAL SENSOR WITH VARIABLE VOLUME SENSOR CELL AND METHOD

[75] Inventor: Ganapati R. Mauze, Sunnyvale, Calif.

[73] Assignee: Hewlett-Packard Company, Palo Alto, Calif.

[21] Appl. No.: 520,428

[22] Filed: Aug. 29, 1995

[51] Int. Cl.⁶ ..................................................... A61B 5/00
[52] U.S. Cl. ...................... 128/634; 128/665; 422/87.07; 422/82.06
[58] Field of Search ............................ 128/634, 633–35, 128/664–65; 422/82–82.11

[56] References Cited

U.S. PATENT DOCUMENTS

| | | |
|---|---|---|
| 4,785,814 | 11/1988 | Kane et al. . |
| 5,096,671 | 3/1992 | Kane et al. ........................ 128/634 X |
| 5,154,890 | 10/1992 | Mauze et al. . |
| 5,176,882 | 1/1993 | Gray et al. . |
| 5,305,744 | 4/1994 | Pfeiffer et al. ........................ 128/634 |
| 5,393,493 | 2/1995 | Makino et al. . |
| 5,423,320 | 6/1995 | Salzman et al. ..................... 128/634 X |
| 5,434,084 | 7/1995 | Burgess, Jr. ........................ 128/634 X |

OTHER PUBLICATIONS

Robert Kok and Pat Hogan, "The Development of an In Situ Fermentation Electrode Calibrator", Biosensors 3 (1987/88) pp. 89–100.

*Primary Examiner*—Angela D. Sykes
*Assistant Examiner*—Ryan Carter

[57] ABSTRACT

A chemical sensor having a sheath, an optical fiber bundle, a mirror, and a mechanism associated with the optical fiber bundle for detecting light interaction, wherein the optical fiber means or the mirror is slidably disposed in the sheath, is provided. At least a portion of the sheath is permeable to a fluid suspected of containing a target chemical. The optical fiber bundle has a portion disposed in the sheath for emitting light to cause optical interaction with the target chemical surrounded by the sheath. The mirror is disposed in the sheath to reflect light emitted by the optical fiber bundle.

12 Claims, 3 Drawing Sheets

CHEMICAL SENSOR WITH VARIABLE VOLUME SENSOR CELL AND METHOD

FIELD OF THE INVENTION

The present invention relates to chemical sensors and methods for analyzing target chemicals in a liquid. More particularly, the present invention relates to chemical sensors that can be used in a liquid containing particulate matters and methods of using and making such chemical sensors.

BACKGROUND

Chemical analyses are often important in evaluating the characteristics and contents of a liquid. For example, in caring for a critically ill patient, it is desirable to know the concentrations of, for example, gases (oxygen, carbon dioxide, etc.) and ions (potassium, calcium, etc.) in the patient's blood. Another example is the culturing of cells, such as in fermentation (e.g., for the production of bacterial antibiotics). In such instances, the levels of nutrients and gases in the liquid are monitored to provide a suitable environment for cell growth and the production of desired products.

Chemical sensors have been used in measuring chemical parameters in liquids. For example, U.S. Pat. No. 4,785,814 (Kane) discloses an optical probe for measuring pH and oxygen content in blood in a blood vessel within a living body. The optical probe has an elongated flexible optical fiber, the distal end of which is adapted to be inserted into a blood vessel. A membrane constructed of a hydrophilic porous material containing a pH sensitive dye is secured to the distal end of the optical fiber. This membrane receives light from the optical fiber and returns light therethrough to the proximal end of the fiber. Another example of using an optical fiber in a chemical sensor is disclosed in U.S. Pat. No. 5,176,882 (Gray et. al.). The chemical sensor described by Gray et. al. is capable of sensing more than one analyte. This sensor has two fiber optic sensor cells, one of which is for measuring a combination of ionic species. A second fiber optic sensor cell is used for measuring gaseous species. Each of the sensor cells has a membrane that is permeable to the corresponding ions and gases of interest.

Although the above chemical sensors are described as being suitable for use with physiological samples, they will not function properly in highly dispersive media (i.e., liquids containing particulate matters) such as fermentation broths, sewage treatment streams, contents of fluidised bed reactors, and slurries. A fermentation electrode calibrator has been described by Kok and Hogan (*Biosensors* 3, 89–100, (1987/88)). This calibrator (with an oxygen probe) is described as being suitable for use in situ in a fermentor. Scrubbing tubes directed at a face of the oxygen probe provide high velocity jets (of air or steam) for cleaning. However, the calibrator of Kok and Hogan is mechanically complex and bulky, making it unsuitable for use in a small liquid sample. What is needed is a chemical sensor of relatively simple mechanical construction for application in a liquid with particulate matters.

SUMMARY

The present invention provides a chemical sensor that can be used to analyze analytes (i.e., target chemicals) dissolved in a sample liquid (i.e., the volume of liquid to be analyzed) that has a liquid (i.e., solvent) and particulate matters (for example, fermentation broths, pond water for environmental analysis, etc.). The chemical sensor has a sheath (or filter) that has at least a portion permeable to the liquid. An optical fiber and mirror arrangement introduces light into the chemical sensor to interact with the analytes in the sample liquid and reflects light through the optical fiber arrangement out of the chemical sensor. The optical fiber and the mirror are disposed in the sheath such that one or both can be slid along the sheath. This slidable movement can be used to force fluid into or out of the chemical sensor through the sheath. The sheath, which generally is impervious to particulate matters, prevents them from entering the chemical sensor. After a certain amount of fluid has been filtered through the sheath and collected inside the chemical sensor, the fluid can be forced through (to back flush) the sheath to dislodge the particulate matters that have accumulated on the outer surface of the sheath. By doing so, the filtration (or permeability) capability of the sheath can be restored to an acceptable degree so that another sample fluid can be analyzed. Methods of using and making the chemical sensor are also provided in the present invention.

Because of the ability of the chemical sensor of the present invention to dislodge particulate matters from its outer surface, it can be advantageously used to analyze analytes in dispersive media (i.e., liquids with particulate matters). Furthermore, since the driving force for dislodging the particulate matters comes from within the sensor, no external structure is needed to direct any cleaning fluid toward the sheath. The chemical sensor is mechanically simple and can be made relatively small. Therefore, it can be used in a small volume of sample liquid and in a congested space. This is particularly beneficial in situations wherein in situ cleaning is desired, for example, in fermentation monitoring. In such instances, because of the need to prevent contamination and maintain isolation of the content of the fermentor, it will be extremely difficult to remove the chemical sensors from the fermentor for cleaning. The use of small, mechanically simple chemical sensors and the ability to repeatedly use the same sensors without removal from the fermentors for cleaning, as provided by the present invention, can provide valuable information without taking too much room or risking the introduction of foreign matters into the sample liquid. The slender and somewhat flexible nature of optical fibers render them uniquely appropriate for transmitting information in and out of the chemical sensor and yet capable of maintaining fluid-tight seal with the sheath as the optical fiber bundle slides relative to the sheath. Likewise, in an embodiment wherein the mirror is located at an end of an optical fiber, it can be slid relative to the sheath in a similar manner.

BRIEF DESCRIPTION OF THE DRAWING

The following figures, which show the embodiments of the present invention, are included to better illustrate the chemical sensors of the present invention. In these figures, wherein like numerals represent like features in the several views, and wherein features are not dram to scale.

DETAILED DESCRIPTION OF THE PREFERRED EMBODIMENTS

The chemical sensor of the present invention has a feature for cleaning particulate matters from the outer surface of a sheath of the chemical sensor by forcing a fluid through the sheath.

Figure 1:
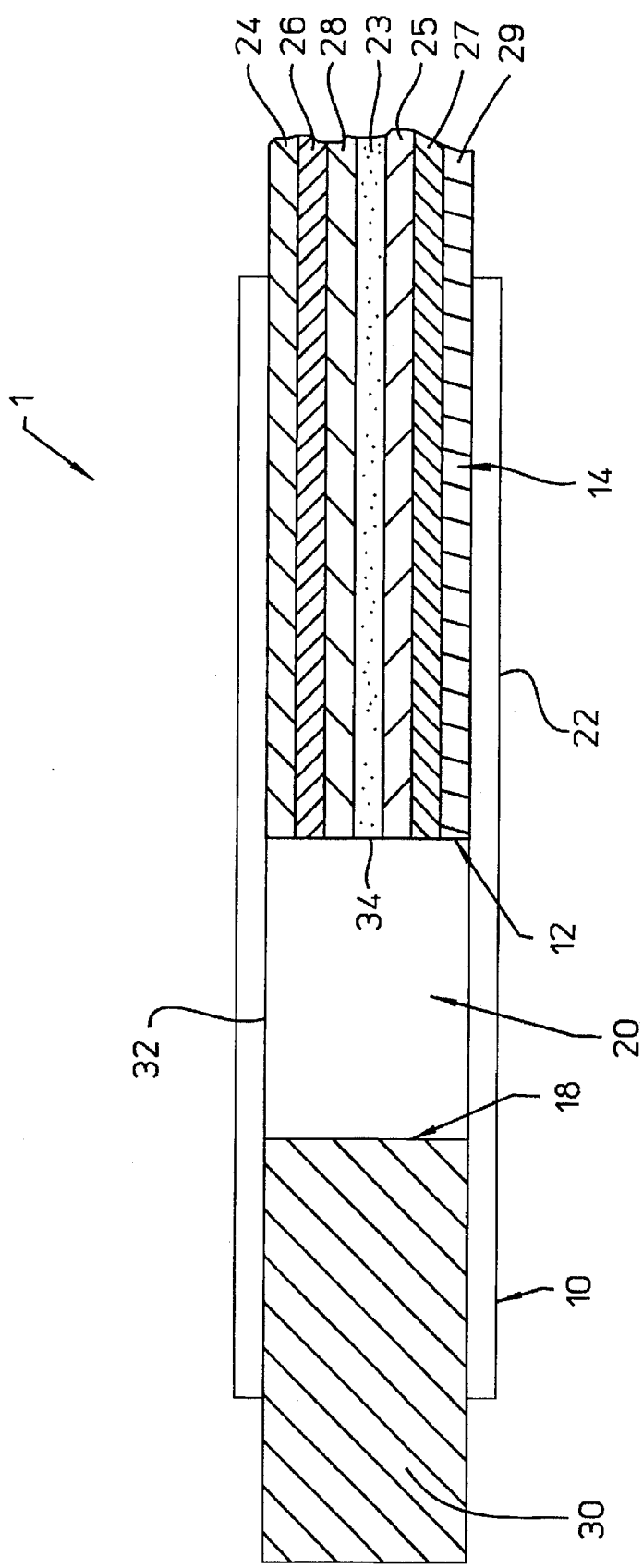
FIG. 1 a schematic representation of a sectional view of an embodiment of the chemical sensor of the present invention.

FIG. 1 is a schematic representation of a preferred embodiment of the chemical sensor of the present invention. The chemical sensor 1 has a sheath 10 that is permeable to a fluid (or solvent) suspected of containing a target chemical (in a dissolved form) to be analyzed. An optical fiber bundle 12 is slidably associated with the sheath 10 so that an interfacing portion 14 of the bundle is slidably disposed in (or encircled or surrounded by) the sheath. In other words, the optical fiber bundle 12 can slide on the inside surface of the sheath 10. A mirror (or reflector) 18 is disposed inside the sheath 10 for reflecting light emitted from the interfacing end 34 of the optical fiber bundle 12. As used herein, the term "interfacing portion" or "interfacing end" refer to the portion or end of the optical fiber or optical fiber bundle that is proximate to the mirror.

The sheath can be made of any appropriate material to provide a filtration capability (i.e., act as a filter) for the removal of particulate matters. It may be made of, for example, fibrous or membranous materials. Materials suitable for making filters that can remove particulate matters from liquid samples are known in the art. Preferably, the sheath is hollow, cylindrical, and made of a membrane that is permeable to the fluid, which is preferably a liquid, containing the target chemical. Often, for example, in fermentation, food processing, environmental analysis, etc., the fluid containing the analyte (target chemical) will be water. However, it is contemplated that the sheath can be selected from appropriate materials so that other liquid samples (such as organic liquids, e.g., ethanol, toluene) containing a target chemical can be analyzed with a chemical sensor containing an appropriate sheath. The sheath 10 is constructed so that it preferably is selectively permeable to a dissolved chemical of molecular weight from about 10 Daltons to 100,000 Daltons. Such filters (or membranes) will allow molecules and ions as small as $H_3O^+$ and as large as penicillin to pass through. More preferably, to maintain a longer useable life, the sheath is made of a material that is porous to allow passage of substances smaller than the smallest undesirable particulate in the medium (e.g., 0.2 μm in bacterial culture media or 0.4 μm in blood sample) and is impervious to larger particulate matters. Such filters will keep out particles the size of bacteria (about 0.2 μm) and larger. In this way, when the chemical sensor is placed in a sample fluid containing particulate matters and the fluid is passed through the sheath 10 into a compartment (or sensor cell or sample region) 20, the particulate matters larger than the pore size will be retained on the outer surface 22 of the sheath 10. This kind of chemical sensors can be used, for example, in a fermentor to monitor a fermentation process. In many cases, a sheath that is impervious to particulate matters of larger than about 2 μm will be adequate to remove dirt, sand, etc. Such a chemical sensor can be useful in environmental analysis.

The optical fiber bundle 12 contains one or more optical fibers (e.g., fibers 23–29). In this embodiment, the interfacing portion 14 of the optical fiber bundle 12 is slidably disposed in the sheath 10 to effect a fluid-tight seal. The optical fiber(s) can be embedded in a suitable material (e.g., a polymer, glass, etc.) to form a structure that conforms to the cross-sectional shape of the sheath to prevent leakage of fluid around the optical fiber bundle. Additionally and optionally, supporting structures, such as a steel wire, and other mechanisms (e.g., a fiber for conducting ultrasonic waves) can also be incorporated in the optical fiber bundle 12. If desired, different optical fibers can be used for transmitting light into and out of the sample region.

In the preferred embodiment of FIG. 1, the mirror 18 is firmly secured inside the sheath so that it is fluid-tight around the mirror. In this way, the optical fiber bundle 12, the mirror 18, and the inner surface 32 of the sheath 10 confines the sample region 20. The sample region 20 is fluid-tight except through the sheath which is permeable to the liquid. The mirror 18 and the optical fiber bundle 12 are so arranged in the sheath that the mirror reflects light emitted by the interfacing end of the optical fiber bundle 12 back to the optical fiber bundle. Light emitted by the optical fiber bundle 12 interacts (i.e., by absorption, fluorescence, etc.) with the target chemical. Light emitted in the light interaction (optical interaction) can also be reflected by the mirror 18 to the optical fiber bundle 12.

Fluid can be passed into the sample region 20 by sliding the optical fiber bundle 12 in a direction away from the mirror to create a negative pressure in the sample region relative to the outside surface 22 of the sheath 10. As fluid is driven through the sheath into the sample region 20 by the pressure differential across the sheath, particulate matters larger than the pores of the sheath will be retained by the sheath, depositing on the outer surface 22 thereof. On the other hand, the optical fiber bundle 12 can be pushed towards the mirror 18 to decrease the volume of the sample region 20. This increases the pressure in the sample region 20 and drives the fluid through the sheath 10 to its outer surface 22. As the fluid traverses through the sheath 10, it dislodges the particulate matters deposited on the outer surface 22 of the sheath, thereby cleaning the sheath to restore at least some of the filtering capacity so that a new sample of fluid can be driven into the sample region 20 to be analyzed.

Preferably, when the outer surface 22 of the sheath 10 is to be cleaned, the optical fiber bundle 12 is pushed so that it abuts the mirror 18 to minimize residual fluid retained in the sample region 20 so that a new sample can be dram therein for analysis with little or no dilution by the old sample residue. Optionally, the mirror can be associated with a fiber (e.g., optical fiber) that extends from inside the sheath 10 to the outside in a direction opposite to that of the optical fiber bundle. This enables the mirror to be slid in the sheath in a fluid-tight manner to facilitate moving fluid in or out of the sample region 20 through the sheath 10.

The sheath can be made of a material so that it is impervious to a selected liquid but is permeable to a gaseous target chemical. The gaseous target chemical that is dissolved or contained in the selected liquid can be analyzed by passing the gaseous target chemical into the sample region by pervaporation. Gases that can be analyzed in this matter include, but are not limited to, methanol, ethanol, acetone, etc. A volume of such gaseous material that accumulates in the sample region 20 can then be forced through the sheath 10 to dislodge particulate matters deposited on the outer surface 22 of the sheath. Gases and permeable membrane combinations that permit pervaporation are known in the art.

It is preferred that the sheath is constructed such that it has the mechanical integrity to maintain its shape when fluid is passed in and out of the sample region 20 through the sheath 10. The dimensions of the sheath 10 are selected, depending on, for example, the pore size, porosity, permeability, and the amount and the size of the particulate matters in the fluid sample. The dimensions are selected such that the particulate matters of selected sizes can be excluded by the sheath and the mechanical integrity of the chemical sensor can be maintained through cycles of filtration and cleaning. Preferably, the sheath is made of a polymer, examples of which include but are not limited to polysulfone, polypropylene, cellulosic polymer, silicone rubber or its derivative, polyethylene, and a composite thereof. The sheath can also be made of an inorganic membrane such as a porous ceramic. For example, the sheath can be about 50 µm to 10 mm thick and about 5 mm to 50 mm in diameter for a polymeric membrane of 0–80% porosity, 0.2 µm (nominal) pores, for use in an aqueous media. The distance between the mirror and the interfacing end 34 of the optical fiber bundle is selected so that an adequate amount of fluid can be collected in the sample region 20 for analysis and an adequate amount of light can be emitted from the optical fiber bundle 12 and reflected by the mirror 18 such that adequate light interaction (of excitation light with the target chemical in the sample) results to enable analysis. For example, the distance can be about 5.0 µm to 500 or more µm in the above chemical sensor.

Figure 2:
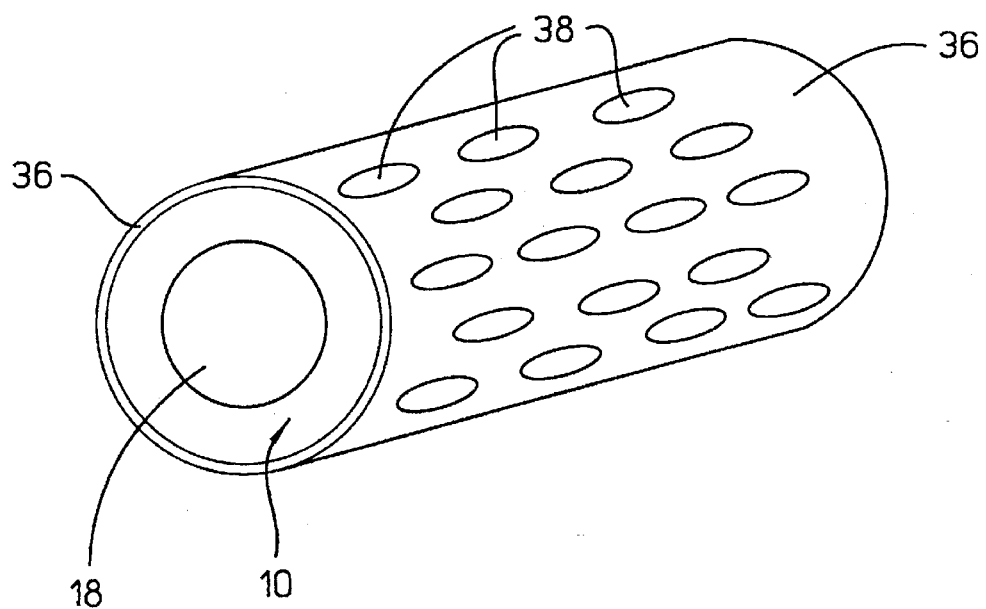
FIG. 2 shows an isometric view of a portion of another embodiment of the chemical sensor in the present invention.

If desired, as shown in FIG. 2, a supporting structure 36, having openings 38 can be used for supporting the sheath. The openings 38 allow fluid to access the sheath. In FIG. 2, the supporting structure 36 is generally cylindrical, tubular and conforms to the outer surface 22 of the sheath 10 so that when fluid is forced through the sheath to clean the outer surface thereof by back-flushing, the supporting structure 36 prevents the outwardly directing pressure from substantially increasing the diameter of the sheath. Likewise, a supporting structure can be disposed on the inner surface 32 to support the sheath when fluid is driven into the sample region 20.

Figure 3:
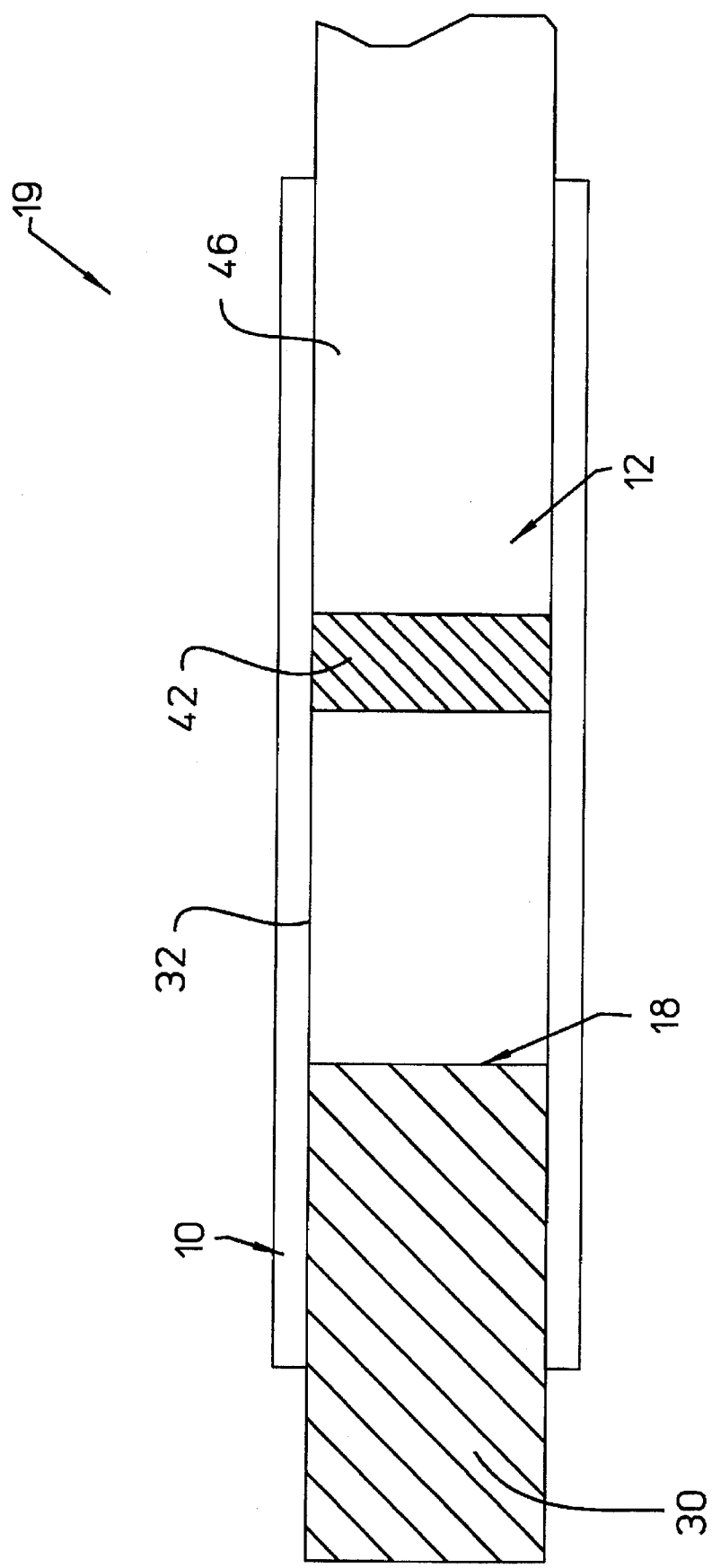
FIG. 3 is a schematic representation of a sectional view of another embodiment of the chemical sensor in the present invention.

FIG. 3 shows an embodiment of a chemical sensor 19 of the present invention wherein a sensing matrix (e.g., sensing matrix 42 on the optical fiber 46) is disposed at the tip of at least one optical fiber of the optical fiber bundle 12. The sensing matrix (or matrices) is selected to be sensitive to one or more of the target chemicals (analytes) of interest. Although it is preferable to dispose the sensing matrices at the tips of the optical fibers, other configurations, such as on the sides of the optical fibers, can also be used. Techniques for using sensing matrices for detecting specific target chemicals are known in the art (e.g., U.S. Pat. No. 5,176, 882, issued to Gray et. al., the dyes and methods of application disclosed by Gray, et at. are incorporated by reference herein). Typically, a sensing matrix has a doped polymer which immobilizes a fluorescence dye sensitive to the target chemical of interest. Light emitted by the optical fiber bundle 12, when interacts with (excites) the target chemical, results in a change in either light intensity or wavelength. This change is transmitted through the optical fiber(s) in the optical fiber bundle 12 to a detector (not shown in the figures) such as a spectrum analyzer.

Figure 4:
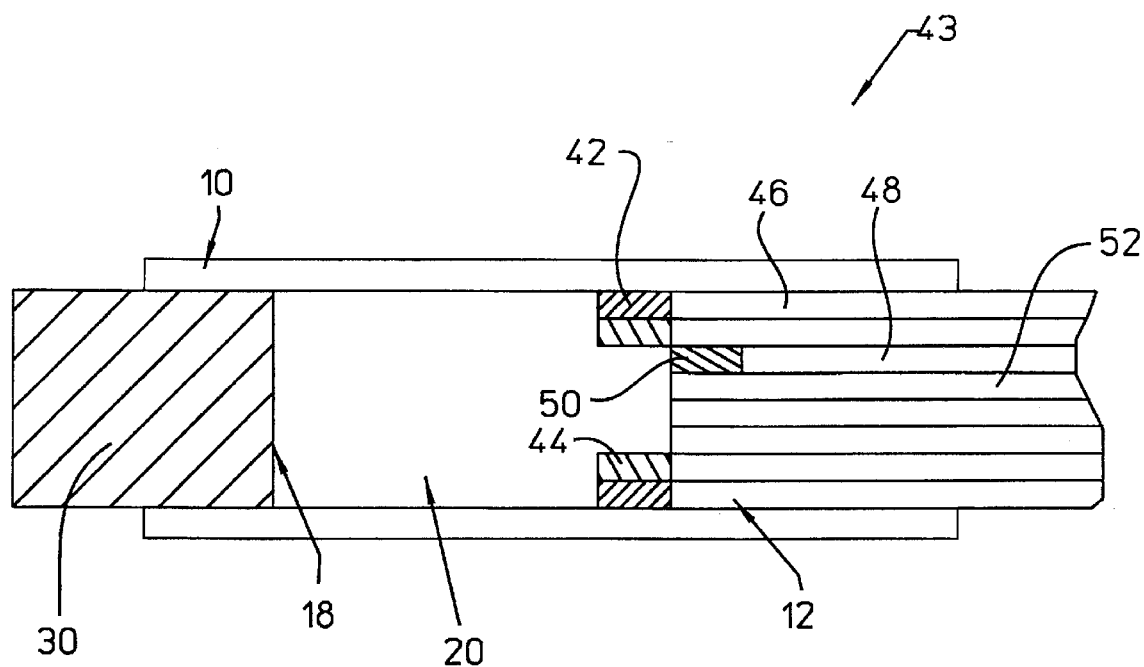
FIG. 4 is a schematic representation of a sectional view of yet another embodiment of the chemical sensor in the present invention.

FIG. 4 shows an embodiment of the chemical sensor of the present invention in which more than one sensing matrices are located at the tips of optical fibers. This chemical sensor 43 allows the detection of more than one target chemical. For example, the sensing matrix 42 is sensitive to pH and potassium ion while sensing matrix 44 is sensitive to oxygen. Additionally, the optical fibers in the optical fiber bundle 12 can be arranged such that their interfacing ends are each at a different distance from the mirror 18. This is done to optimize the signal to noise ratio in the detection of different target chemicals in which lights of different wavelengths are involved. This is because the balance of the need to have an adequate amount of the target chemical present and the need for an adequate amount of excitation lights may be different for different target chemicals. For example, optical fiber 46 and optical fiber 48 are disposed in the sheath such that their corresponding sensing matrices 42 and 50 are at different distances from the mirror 18. Also, some of the fibers (e.g., fiber 52) need not have any sensing matrix disposed at the tip thereof. Such bare fibers can be used to conduct light from the sample region 20 to perform remote spectroscopy. Such remote spectroscopy can be done by using additional analytical equipment (not shown) at a site remote from the chemical sensor.

By using the chemical sensor of the present invention, the presence of target chemical(s) can be analyzed. The intensity of the light interaction can be detected and analyzed to obtain information on the concentration of target chemical (s). Although the illustrative embodiments of the present invention have been described in detail, it is to be understood that the above-described embodiments can be modified by one skilled in the art, especially in sizes and shapes and combinations of various described features, without departing from the spirit and scope of the invention. For example, instead of the optical fiber bundle or the mirror, both the optical fiber bundle and the mirror can be slid along the sheath to force fluid through the sheath. A mechanized (e.g., motorized, pneumatic) means can be used to drive the sliding movement. Also, an optical fiber can be used for transmitting light both to and from the sample region.

What is claimed is:

1. A chemical sensor, comprising:
   (a) a sheath, having at least a portion permeable to a fluid suspected of containing a target chemical, for surrounding a sample of said fluid;
   (b) an optical fiber means having a portion disposed in the sheath for emitting light to cause light interaction with the target chemical in the sample of said fluid surrounded by the sheath;
   (c) a mirror disposed in the sheath for reflecting light emitted by the optical fiber means; and
   (d) means associated with the optical fiber means for detecting the light interaction;
   wherein the sheath, optical fiber means, and mirror define a chamber for including the fluid and wherein at least one of the optical fiber means and the mirror is slidably disposed in the sheath to force the fluid through the sheath.

2. The chemical sensor according to claim 1 wherein the optical fiber means is slidably disposed in the sheath.

3. The chemical sensor according to claim 1 wherein the sheath is a membrane permeable to the fluid but impervious to particulate matters.

4. The chemical sensor according to claim 2 wherein the membrane is permeable to molecules smaller than 100,000 Daltons molecular weight.

5. The chemical sensor according to claim 1 wherein the sheath is impervious to particulate matters of larger than 2.0 µm.

6. The chemical sensor according to claim 1 wherein the sheath is impervious to particulate matters of larger than 0.2 µm.

7. The chemical sensor according to claim 1 wherein the optical fiber means has at least 2 optical fibers each having a different sensing matrix disposed thereon for sensing the light interaction.

8. The chemical sensor according to claim 1 wherein the optical fiber means has at least 2 optical fibers each disposed at a different distance from the mirror.

9. The chemical sensor according to claim 1 further comprising a porous support surrounding the sheath for supporting the sheath as fluid is forced therethrough from a location surrounded by the sheath.

10. The chemical sensor according to claim 1 wherein at least one of the optical fiber means and the mirror is slidably disposed in the sheath to increase the pressure in the chamber to force the fluid through the sheath to dislodge particulate matters on the sheath outside the chamber.

11. The chemical sensor according to claim 1 wherein at least one of the optical fiber means and the mirror is slidably disposed in the sheath to decrease the pressure in the chamber to force the fluid through the sheath into the chamber while keeping out particulate matters.

12. A chemical sensor, comprising:
   (a) a sheath, having at least a portion permeable to a fluid suspected of containing a target chemical, for surrounding a sample of said fluid, the sheath being a membrane permeable to the fluid but impervious to particulate matters;
   (b) an optical fiber means having a portion disposed in the sheath for emitting light to cause light interaction with the target chemical in the sample of said fluid surrounded by the sheath;
   (c) a minor disposed in the sheath for reflecting light emitted by the optical fiber means; and
   (d) means associated with the optical fiber means for detecting the light interaction;

wherein the sheath, optical fiber means, and mirror define a chamber for including the fluid and wherein at least one of the optical fiber means and the mirror is slidably disposed in the sheath to vary the volume and pressure in the chamber such that the fluid is forced through the sheath into the chamber while keeping out the particulate matters when the volume of the chamber is increased and to dislodge particulate matters on the sheath outside the chamber when the volume of the chamber is reduced.

* * * * *